United States Patent [19]

Gaffar et al.

[11] Patent Number: 5,531,982
[45] Date of Patent: *Jul. 2, 1996

[54] ANTIMICROBIAL ORAL COMPOSITION

[75] Inventors: Abdul Gaffar, Princeton; Nuran Nabi, Cranbury; John Afflitto, Brookside, all of N.J.

[73] Assignee: Colgate Palmolive Company, New York, N.Y.

[*] Notice: The term of this patent shall not extend beyond the expiration date of Pat. No. 5,032,386.

[21] Appl. No.: 275,469

[22] Filed: Jul. 14, 1994

Related U.S. Application Data

[60] Continuation-in-part of Ser. No. 161,033, Dec. 3, 1993, which is a division of Ser. No. 981,723, Nov. 25, 1992, Pat. No. 5,344,641, which is a division of Ser. No. 754,887, Sep. 6, 1991, Pat. No. 5,192,530, and Ser. No. 655,571, Feb. 14, 1991, Pat. No. 5,178,851, which is a continuation of Ser. No. 398,566, Aug. 25, 1989, Pat. No. 5,032,386, said Ser. No. 754,887, is a continuation of Ser. No. 398,606, Aug. 25, 1989, abandoned, said Ser. No. 398,566, and Ser. No. 398,606, each is a continuation-in-part of Ser. No.291,712, Dec. 29, 1988, Pat. No. 4,894,220, and Ser. No. 346,258, May 1, 1989, abandoned, said Ser. No. 291,712, and Ser. No. 346,258, each is a continuation-in-part of Ser. No.8,901, Jan. 30, 1987, abandoned.

[51] Int. Cl.$^6$ ............................... A61K 7/16; A61K 7/18
[52] U.S. Cl. ..................... 424/49; 474/52; 474/58
[58] Field of Search ........................... 424/49–58

[56] References Cited

U.S. PATENT DOCUMENTS

| | | | |
|---|---|---|---|
| 3,932,604 | 1/1976 | Barth | 424/49 |
| 3,970,747 | 7/1976 | Barth | 424/52 |
| 5,032,386 | 7/1991 | Gaffar et al. | 424/49 |
| 5,087,887 | 1/1992 | Gaffar et al. | 424/52 |
| 5,089,255 | 2/1992 | Gaffar et al. | 424/52 |
| 5,144,024 | 9/1992 | Pepper et al. | 536/128 |
| 5,178,851 | 1/1993 | Gaffar et al. | 424/52 |
| 5,180,578 | 1/1993 | Gaffar et al. | |
| 5,192,530 | 3/1993 | Gaffar et al. | 424/52 |
| 5,192,531 | 3/1993 | Gaffar et al. | 424/52 |
| 5,288,480 | 2/1994 | Gaffar et al. | 424/52 |
| 5,292,526 | 3/1994 | Gaffar et al. | 424/49 |
| 5,334,375 | 8/1994 | Nabi et al. | 424/52 |

OTHER PUBLICATIONS

Pepper et al Derwent Abstract of U.S. Pat. No. 5,144,024 Sep. 1, 1992.
Colgate Derwent Abstract of U.S. Pat. No. 5,089,255 Feb. 18, 1992.
Rolla et al Derwent Abstract of E.P. 251146 Jan. 7, 1988 C.A. 108:8160.
Goupil et al Derwent Abstract of EP 138705 Apr. 24, 1985 C.A. 103:42417.
Hoffman LaPoche Derwent Abstract of Ger DE 2606533 Aug. 26, 1976 CA. 85:149140.
Colgate/Baeth Derwent Abstracts of U.S. Pat. No. 3,932,604 Apr. 13, 1976 & 3,970,747 Jun. 20. 1976 C.A. 84:95631.
Svanberg Caries Res. 25(6):449–453 (1991) Abstract C.A. 115:270669.
Scheinin Int. Dent. J. 35:50–7 1985 Abstract C.A. 104:128442.
Arends et al Caries Res. 18(4):296–301 (1989) Abstract C.A. 101:108 380.
Tolev et al(I) C.A. 99:218411.
Tolev et al(II) C.A. 98:95484.

*Primary Examiner*—Shep K. Rose
*Attorney, Agent, or Firm*—Robert L. Stone

[57] ABSTRACT

A oral composition which inhibits plaque formation and reduces gingivitis and caries comprising a substantially water insoluble noncationic antimicrobial agent, such as triclosan and an acid reducing agent, such as xylitol. The composition is a dentifrice containing a siliceous polishing agent.

19 Claims, No Drawings

ANTIMICROBIAL ORAL COMPOSITION

BACKGROUND OF THE INVENTION

This application is a continuation-in-part application of application Ser. No. 08/161,033 filed Dec. 3, 1993, which is a divisional application of Ser. No. 07/981,723 filed Nov. 25, 1992, now U.S. Pat. No. 5,344,641 issued Sep. 6, 1994, which is a divisional application of Ser. No. 07/754,887 filed Sep. 6, 1991 now U.S. Pat. No. 5,192,530, granted Mar. 9, 1993, and of Ser. No. 07/655,571 filed Feb. 14, 1991, now U.S. Pat. No. 5,178,851 granted Jan. 12, 1993 which are continuation applications of Ser. No. 07/398,606 filed Aug. 25, 1989, now abandoned, and of Ser. No. 07/398,566 filed Aug. 25, 1989, now U.S. Pat. No. 5,032,386, granted Jul. 16, 1991, respectively, which are continuation-in-part applications of Ser. No. 07/291,712 filed Dec. 29, 1988, now U.S. Pat. No. 4,894,220, granted Jan. 16, 1990, and of Ser. No. 07/346,258 filed May 1, 1989, now abandoned, which are continuation-in-part applications of 07/008,901, filed Jan. 30, 1987, now abandoned.

This invention relates to an antimicrobial oral composition. More particularly, it relates to oral formulations such as dentifrices, mouthrinses, liquid dentifrices, or gels, etc., which can inhibit the formation and/or development of dental caries. In addition, fluoride is an optional ingredient that can be incorporated into the invention to further reduce caries.

Dental plaque is a soft deposit which forms on teeth as opposed to calculus which is a hard calcified deposit on teeth. Unlike calculus, plaque may form on any part of the tooth surface, particularly including at the gingival margin. Hence, besides being unsightly, it is implicated in the occurrence of gingivitis and dental caries.

Furthermore, dental caries formation is a process which occurs due to plaque bacteria metabolizing ingested fermentable carbohydrates to produce acid, which in turn leads to demineralization of the enamel surface of the tooth. In the past, the main approach to reduction of caries has been with the use of fluorides. The main reason for fluorides is believed to be their direct inhibitory effect on enamel demineralization and promotion of the remineralization process. Indeed in U.S. Pat. No. 5,089,255, to Gaffar et al, remineralization is taught to be promoted by fluoride and xylitol.

An alternate or supplemental approach to fluorides is use of agents which effectively inhibit plaque acid production by the bacteria. This can be accomplished either by killing or removing the acidogenic plaque bacteria or by inhibiting their metabolic processes, in particular the fermentation of carbohydrates and glucose. Bacteriocidal compounds can, in theory, accomplish this, if they are suitably formulated and delivered, and have sufficient substantivity and efficacy.

The present invention combines the non-bacteriocidal agent xylitol with a non-cationic antibacterial agent such as, triclosan. Xylitol, although not bacteriocidal, appears to cause a disturbance in the metabolism of fermentable carbohydrate and thereby reduces the production of acid and extracellular polymers characteristic of cariogenic plaque. Xylitol, a sugar alcohol compound has been shown to reduce the amount of acid generated by *S. mutans* in response to glucose and this effect is thought to be related to inhibition of the phosphofuctokinase step of glycolysis. (Assev, S. and Rolla, G.: Further Studies On The Growth And Inhibition Of *Streptococcus Mutans* OMZ 176 by Xylitol. Acta Path. Microbiol. Scand. Sect. B, 94:97–102, 1986).

Studies in humans employing high frequency use of xylitol in candies and gums have reported an effect to reduce dental caries incidence (e.g. Bär, Albert "Caries Prevention with Xylitol"; World Review of Nutrition and Dietetics, vol. 55, 1988). However, it has not been shown in either animal or human studies that xylitol in the absence of another active agent, when used in conventional oral hygiene vehicles, such as dentifrices, according to customary usage frequency, is substantially effective in reducing dental caries incidence compared to a matching placebo. It is a particular finding of this invention that an oral composition formulation which employs xylitol in combination with a particular non-cationic antibacterial agent, halogenated diphenyl ether, such as Triclosan, in a dentifrice having a siliceous polishing agent or in a mouth rinse or gel is effective to reduce caries in animals (rats). Xylitol and halogenated diphenyl ether appear to provide a complementary action in such oral compositions which results in significant caries inhibition.

In companion co-pending U.S. patent application Ser. No. 08/160,337, filed Dec. 1, 1993, belonging to the same party in interest, plaque reduction in a dentifrice containing alkaline earth metal salt polishing agent is achieved by xylitol together with a non-cationic antibacterial agent such as triclosan. This plaque reduction is quite distinct from the ultimate anticaries effect of the present invention relating to an oral composition which is a dentifrice containing a siliceous polishing agent, or a mouthwash or gel.

It is well known that it is highly desirable to include antimicrobial agents which have been known to reduce plaque in oral compositions. Frequently, cationic antibacterial agents have been suggested. For instance, in U.S. Pat. No. 4,022,880 to Vinson et al, a compound providing zinc ions as an anticalculus agent is admixed with an antibacterial agent effective to retard the growth of plaque bacteria. A wide variety of antibacterial agents are described with the zinc compounds including cationic material such as guanides and quaternary ammonium compounds as well as non-cationic compounds such as halogenated salicylanilides and halogenated hydroxydiphenyl ethers. The noncationic antimicrobial halogenated hydroxydiphenyl ether, triclosan, has also been described in combination with zinc citrate trihydrate in European Patent Publication 0161,899 to Saxton et al. Triclosan is also disclosed in European Patent Publication 0271,332 to Davis as a toothpaste component in a carrier system containing a solubilizing agent such as propylene glycol.

The cationic antibacterial materials such as chlorhexidine, benzethonium chloride and cetyl pyridinium chloride have been the subject of greatest investigation as antimicrobial agents. However, they are generally not effective when used with anionic surfactants. Noncationic antibacterial agents such as triclosan, on the other hand, can be compatible with anionic surfactants in an oral composition.

However, oral compositions typically are mixtures of numerous components and even such neutral materials as humectants can affect performance of such components.

Moreover, even noncationic antimicrobial agents may have limited antiplaque effectiveness with commonly used materials such as polyphosphate anticalculus agents which are disclosed together in British Patent Publication 22 00551 of Gaffar et al and in EP 0251591 of Jackson et al. In commonly assigned U.S. Pat. No. 5,180,578 it is shown that the antiplaque effectiveness is greatly enhanced by including an antibacterial-enhancing agent (AEA) which enhances the delivery of said antibacterial agent to, and retention thereof on, oral surfaces, and by providing optimized amounts and ratios of polyphosphate and AEA.

Further, even when polyphosphate anticalculus agent is not present as in commonly assigned U.S. Pat. No. 5,192,530, antiplaque effectiveness on soft oral tissue is optimized by including the AEA and a solubilizing material which dissolves the noncationic antibacterial agent in saliva when the polishing agent is a siliceous polishing agent present in amount of about 5–30%. Indeed, when the amount of noncationic antibacterial agent is optimized, even the special solubilizing material is not required, as in commonly assigned U.S. Pat. No. 5,156,835.

It has been reported that plaque grown in the presence of xylitol is less acidic than plaque grown under control conditions. (Makinen, K. K. "Latest Dental Studies On Xylitol And Mechanism Of Action Of Xylitol In Caries Limitation", Grenby, T. H., Ed; Elsevier Applied Science, pp. 331–362 (1990)).

There are a number of patent disclosures which describe the optional presence of xylitol as a sweetener ingredient or a humectant in oral compositions which contain or may contain a noncationic halogenated diphenyl ether antibacterial agent such as triclosan. These include ancestor U.S. Pat. Nos. 5,192,531; 5,043,154 and 4,894,220 as well as companion U.S. Pat. Nos. 5,192,530; 5,188,821; 5,180,578; 5,178,851; 5,156,835; 5,080,887; 5,037,637; 5,037,635 and 5,032,386. Similar optional disclosures occur in U.S. Pat. Nos. 5,202,111; 5,192,533; 5,096,700; 4,935,227 and 4,927,625, as well as in Lion Dentifrice Company-Japanese Patent Disclosures H2-11511; H3-541 0; H4-13918; and H4-13919. The art did not recognize that xylitol in combination with noncationic halogenated diphenyl ether, antibacterial agent in a dentifrice containing a siliceous polishing agent could provide significant caries inhibition.

SUMMARY OF THE INVENTION

It is an advantage of this invention that an oral composition is provided which is highly effective against cariogenic plaque growth.

It is a further advantage of this invention that an antiplaque oral composition is provided which is effective to reduce the occurrence of caries.

Additional advantages of this invention will be apparent from consideration of the following specification.

In accordance with certain of its aspects, this invention relates to an antimicrobial oral composition comprising an orally acceptable aqueous humectant vehicle, and when said oral composition is a dentifrice, about 10–30% of a dentally acceptable water-insoluble siliceous polishing agent, said oral composition comprising an effective antiplaque amount of a substantially water insoluble noncationic antibacterial agent and at least about 0.1% by weight of xylitol said oral composition containing at least one of a surface active agent and a flavor oil to facilitate dispersion of said antibaterial agent in said composition.

Typical examples of water insoluble noncationic antibacterial agents which are particularly desirable from considerations of effectiveness, safety and formulation are:
Halogenated Diphenyl Ethers
    2',4,4'-trichloro-2-hydroxy-diphenyl ether (Triclosan)
    2,2'-dihydroxy-5,5'-dibromo-diphenyl ether
Halogenated Salicylanilides
    4',5-dibromosalicylanilide
    3,4',5-trichlorosalcylanilide
    3,4',5-tribromosalicylanilide
    2,3,3',5-tetrachlorosalicylanilide
    3,3,3',5-tetrachlorosalicylanilide
    3,5-dibromo-3'-trifluoromethyl salicylanilide
    5-n-octanoyl-3'-trifluoromethyl salicylanilide
    3,5-dibromo-4'-trifluoromethyl salicylanilide
    3,5-dibromo-3'-trifluoromethyl salicylanilide (Fluorophene)

| Benzoic Esters | |
|---|---|
| Methyl | p-Hydroxybenzoic Ester |
| Ethyl | p-Hydroxybenzoic Ester |
| Propyl | p-Hydroxybenzoic Ester |
| Butyl | p-Hydroxybenzoic Ester |

Sesquiterpene Alcohols
    Farnesol
    Nerolidol
    Bisabolol
    Santalol
Halogenated Carbanilides
    3,4,4'-trichlorocarbanilide
    3-trifluoromethyl-4,4'-dichlorocarbanilide
    3,3,4'-trichlorocarbanilide Phenolic Compounds (including phenol and its homologs, mono- and poly-alkyl and aromatic halo (e.g. F, Cl, Br, I)-phenols, resorcinol and catechol and their derivatives and bisphenolic compounds). Such compounds include inter alia:

| Phenol and its Homologs | |
|---|---|
| Phenol | |
| 2 Methyl | Phenol |
| 3 Methyl | Phenol |
| 4 Methyl | Phenol |
| 4 Ethyl | Phenol |
| 2,4-Dimethyl | Phenol |
| 2,5-Dimethyl | Phenol |
| 3,4-Dimethyl | Phenol |
| 2,6-Dimethyl | Phenol |
| 4-n Propyl | Phenol |
| 4-n-Butyl | Phenol |
| 4-n-Amyl | Phenol |
| 4-tert-Amyl | Phenol |
| 4-n-Hexyl | Phenol |
| 4-n-Heptyl | Phenol |
| 2-Methoxy-4-(2-Propenyl)-Phenol (Eugenol) | |
| 2-Isopropyl-5-Methyl - Phenol (Thymol) | |

| Mono- and Poly-Alkyl and Aralkyl Halophenols | |
|---|---|
| Methyl | p-Chlorophenol |
| Ethyl | p-Chlorphenol |
| n-Propyl | p-Chlorophenol |
| n-Butyl | p-Chlorophenol |
| n-Amyl | p-Chlorophenol |
| sec-Amyl | p-Chlorophenol |
| n-Hexyl | p-Chlorophenol |
| Cyclohexyl | p-Chlorophenol |
| n-Heptyl | p-Chlorophenol |
| n-Octyl | p-Chlorophenol |
| O-Chlorophenol | |
| Methyl | o-Chlorophenol |
| Ethyl | o-Chlorophenol |
| n-Propyl | o-Chlorophenol |
| n-Butyl | o-Chlorophenol |
| n-Amyl | o-Chlorophenol |
| tert-Amyl | o-Chlorophenol |
| n-Hexyl | o-Chlorophenol |
| n-Heptyl | o-Chlorophenol |
| p-Chlorophenol | |
| o-Benzyl | p-Chlorophenol |
| o-Benzyl-m-methyl | p-Chlorophenol |

-continued

| | |
|---|---|
| o-Benzyl-m, m-dimethyl | p-Chlorophenol |
| o-Phenylethyl | p-Chlorophenol |
| o-Phenylethyl-m-methyl | p-Chlorophenol |
| 3-Methyl | p-Chlorophenol |
| 3,5-Dimethyl | p-Chlorophenol |
| 6-Ethyl-3-methyl | p-Chlorophenol |
| 6-n-Propyl-3-methyl | p-Chlorophenol |
| 6-iso-propyl-3-methyl | p-Chlorophenol |
| 2-Ethyl-3,5-dimethyl | p-Chlorophenol |
| 6-sec Butyl-3-methyl | p-Chlorophenol |
| 2-iso-Propyl-3,5-dimethyl | p-Chlorophenol |
| 6-Diethylmethyl-3-methyl | p-Chlorophenol |
| 6-iso-Propyl-2-ethyl-3-methyl | p-Chlorophenol |
| 2-sec Amyl-3,5-dimethyl | p-Chlorophenol |
| 2-Diethylmethyl-3,5-dimethyl | p-Chlorophenol |
| 6-sec Octyl-3-methyl | p-Chlorophenol |
| p-Bromophenol | |
| | |
| Methyl | p-Bromophenol |
| Ethyl | p-Bromophenol |
| n-Propyl | p-Bromophenol |
| n-Butyl | p-Bromophenol |
| n-Amyl | p-Bromophenol |
| sec-Amyl | p-Bromophenol |
| n-Hexyl | p-Bromophenol |
| cyclohexyl | p-Bromophenol |
| o-Bromophenol | |
| | |
| tert-Amyl | o-Bromophenol |
| n-Hexyl | o-Bromophenol |
| n-Propyl-m,m-Dimethyl | o-Bromophenol |
| 2-Phenyl Phenol | |
| 4-Chloro-2-methyl phenol | |
| 4-chloro-3-methyl phenol | |
| 4-chloro-3,5-dimethyl phenol | |
| 2,4-dichloro-3,5-dimethyl phenol | |
| 3,4,5,6-tetrabromo-2-methyl-phenol | |
| 5-methyl-2-pentylphenol | |
| 4-isopropyl-3-methylphenol | |
| 5-chloro-2-hydroxydiphenyl methane | |

Resorcinol and Its Derivatives

Resorcinol

| | |
|---|---|
| Methyl | Resorcinol |
| Ethyl | Resorcinol |
| n-Propyl | Resorcinol |
| n-Butyl | Resorcinol |
| n-Amyl | Resorcinol |
| n-Hexyl | Resorcinol |
| n-Heptyl | Resorcinol |
| n-Octyl | Resorcinol |
| n-Nonyl | Resorcinol |
| Phenyl | Resorcinol |
| Benzyl | Resorcinol |
| Phenylethyl | Resorcinol |
| Phenylpropyl | Resorcinol |
| p-Chlorobenzyl | Resorcinol |
| 5-Chloro | -2,4-Dihydroxydiphenyl Methane |
| 4'-Chloro | -2,4-Dihydroxydiphenyl Methane |
| 5-Bromo | -2,4-Dihydroxydiphenyl Methane |
| 4'-Bromo | -2,4-Dihydroxydiphenyl Methane |

Bisphenolic Compounds

Bisphenol A 2,2'-methylene bis (4-chlorophenol)

2,2'-methylene bis (3,4,6-trichlorophenol) (hexachlorophene)

2,2'-methylene bis (4-chloro-6-bromophenol)

bis (2-hydroxy-3,5-dichlorophenyl) sulfide bis (2-hydroxy-5-chlorobenzyl) sulfide The noncationic antibacterial agent is present in the dentifrice in an effective antiplaque amount, typically about 0.01–5% by weight, preferably about 0.03–1.0% and most preferably about 0.3–0.5%. The antibacterial agent is substantially water-insoluble, meaning that its solubility is less than about 1% by weight in water at 25° C. and may be even less than about 0.1%.

The preferred halogenated diphenyl ether and most preferred noncationic antibacterial agent is triclosan. Preferred other noncationic antibacterial agents are hexyl resorcinol and 2,2'methylene bis (4-chloro-6-bromophenol).

Triclosan is disclosed in U.S. Pat. No. 4,022,880 as an antibacterial agent in combination with an anticalculus agent which provides zinc ions and in German Patent Disclosure 3532860 in combination with a copper compound. In European Patent Disclosure 0278744 it is disclosed in combination with a tooth desensitizing agent containing a source of potassium ions. It is also disclosed as an antiplaque agent in an oral composition formulated to contain a lamellar liquid crystal surfactant phase having a lamellar spacing of less than 6.0 nm and which may optionally contain a zinc salt in published European Patent Application 0161898 of Lane et al and in a dentifrice containing zinc citrate trihydrate in published European Patent Application 0161899 to Saxton et al.

Xylitol, which enhances the anticariogenic and antiplaque properties in combination with the noncationic antibacterial agent may be employed in amounts ranging upward from about 0.1% by weight for instance to about 40%. In amounts ranging upward from 0.1% by weight to about 5% or more it provides desirable sweetening to the oral composition when present as the only sweetener or desirably when mixed with another sweetener. It also provides desirable humectant character to the oral composition and can be the sole humectant particularly when present in amounts of about 20–40%, although it is desirably mixed with another humectant. Preferably xylitol is present in amount of about 1–30% by weight, more preferably about 3–25%, and most preferably about 5–20%.

In this invention, the oral composition dentifrice may be substantially a dental cream, toothpaste or gel dentifrice, containing a siliceous polishing agent which could be transparent, translucent or opacified, or a mouthwash or dental gel, which does not contain a polishing agent. Preferred siliceous polishing materials in dentifrices include crystalline silica having particle sized of up to about 5 microns, a mean particle size of up to about 1.1 microns, and a surface area of up to about 50,000 $cm^2/gm$, silica gel or colloidal silica and complex amorphorous alkali metal aluminosilicate.

When visually clear or opacified gels are employed, a polishing agent of colloidal silica, such as those sold under the trademark SYLOID as Syloid 72 and Syloid 74 or under the trademark SANTOCEL as Santocel 100 or alkali metal aluminosilicate complexes (that is, silica containing alumina combined in its matrix) are particularly useful, since they are consistent with gel-like texture and have refractive indices close to the refractive indices of gelling agent-liquid (including water and/or humectant) systems commonly used in dentifrice.

The polishing material is generally present in the oral composition dentifrices such as toothpaste cream paste or gel compositions in weight concentrations of about 5% to about 30%.

In embodiments of oral compositions, an orally acceptable vehicle including a water-phase with humectant is present. As stated, xylitol can be the sole humectant, although it is preferably mixed with another humectant, preferably glycerine and/or sorbitol. In a dentifrice, water is present typically in amount of about 3% to 40% by weight, more typically about 10%–35%, and humectant typically in amount of about 6.5%–80%, such as about 10%-80%, preferably about 20%–75% by weight of the oral composition, more typically about 25–60%. Xylitol can be the sole humectant in amounts of about 20%–40% by weight or can be mixed with additional humectant with humectant amounts of about 20%–75% by weight total humectants. Reference hereto to sorbitol refers to the material typically as available commercially in 70% aqueous solutions. In clear gels where the refractive index is an important consideration, about 3–30% of water, 0% to about 70% of glycerine and about 20–25% of sorbitol are preferably employed.

The oral composition dentifrices and dental gels typically contain a natural or synthetic thickener or gelling agent in proportions of about 0.1 to about 10% by weight, preferably about 0.5 to about 5% in a dentifrice and about 4–10% in a dental gel. A suitable thickener is synthetic hectorite, a synthetic colloidal magnesium alkali metal silicate complex clay available for example as Laponite (e.g. CP, SP 2002,/D) marketed by Laporte Industries Limited. Laponite D analysis shows, approximately by weight, 58.00% $SiO_2$, 25.40% MgO, 3.05% $Na_2O$, 0.98% $Li_2O$, and some water and trace metal. Its true specific gravity is 2.53 and it has an apparent bulk density (g./ml. at 8% moisture) of 1.0.

Other suitable gelling agents or thickeners include Irish moss, i-carragenan, gum tragacanth, starch, polyvinylpyrrolidone, hyroxyethylpropyl cellulose hydroxybutyl methyl cellulose, hydroxypropyl methyl cellulose hydroxyethyl cellulose (e.g. available as Natrosol), sodium carboxymethyl cellulose, and colloidal silica such those available as finely ground Syloid 244 and Sylox 15.

When the oral composition is a mouthwash, the oral vehicle includes at least one of a surface-active agent, a flavoring oil and also a non-toxic alcohol which also assists in dissolving the antibacterial agent.

In the aspect of the present invention wherein the oral composition is a mouthwash or liquid dentifrice, substantially liquid in character, and the vehicle particularly in a mouthwash is typically a water-alcohol mixture. Generally, the weight ratio of water to alcohol is in the range of from about 1:1 to about 20: 1, preferably about 3:1 to 10:1 and more preferably about 4:1 to about 6:1. The total amount of water-alcohol mixture in this type of preparation is typically in the range of from about 70 to about 99.9% by weight. The alcohol is a non-toxic alcohol such as ethanol or isopropanol. Humectant such as glycerine and sorbitol may be present in amount of about 10–30% by weight. Liquid dentifrices typically contain about 50–85% of water, may contain about 0.5-20% by weight of non-toxic alcohol and may also contain about 10–40% by weight of humectant such as glycerine and/or sorbitol. Reference herein to sorbitol refers to the material typically as available commercially in 70% aqueous solutions. Ethanol is the preferred nontoxic alcohol. The alcohol is believed to assist in dissolving the water-insoluble non-cationic antibacterial agent as, it is believed, also does flavoring oil.

In a dental gel water is typically present in the vehicle in amount of about 30–80% and humectant in amount of about 20–65%, each by weight of the composition.

The pH of such oral composition of the invention is generally in the range of about 4.5 to about 9 or 10 and preferably about 6.5 to about 7.5 or 8. It is noteworthy that the compositions of the invention may be applied orally at a pH below 5 without substantially decalcifying or otherwise damaging dental enamel. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc.).

The oral composition has anticaries effectiveness even without a fluoride ion source. However, it may also contain an anticaries amount of a fluoride ion source sufficient to supply about 25 ppm to 5000 ppm of fluoride ions to improve anticaries effectiveness, particularly with respect to reducing smooth surface caries, preferably from 250 ppm to 1500 ppm.

The sources of fluoride ions, or fluorine-providing component are well known in the art as anti-caries agents. These compounds, when present, may be slightly soluble in water or may be fully water-soluble. They are characterized by their ability to release fluoride ions in water and by substantial freedom from undesired reaction with other compounds of the oral preparation. Among these materials are inorganic fluoride salts, such as soluble alkali metal, alkaline earth metal salts, or example sodium fluoride, potassium fluoride, ammonium fluoride, a copper fluoride such as cuprous fluoride, zinc fluoride, sodium flourosilicate, ammonium fluorosilicate, sodium fluorozirconate, sodium fluorozirconate, sodium monofluorophosphate, aluminum mono-and di-fluorophosphate and fluorinated sodium calcium pyrophosphate. Alkali metal and tin fluorides, such as sodium and stannous fluorides, sodium monofluorophosphate (MFP) and mixtures thereof, are preferred.

In the present invention the antiplaque effectiveness of the noncationic antibacterial agent is substantially enhanced in the presence of xylitol and water-insoluble siliceous polishing agent, even when a special antibacterial-enhancing agent (AEA) is not present.

When present, the antibacterial-enhancing agent which can further enhance delivery of the noncationic antibacterial agent to, and retention thereof on, oral surfaces, is employed in amounts effective to achieve such enhancement within the range in the oral composition of about 0.05% to about 4%, preferably about 0.1% to about 3%, more preferably about 0.5% to about 2.5% by weight.

The AEA may be a simple compound, preferably a polymerizable monomer, more preferably a polymer, which latter term is entirely generic, including for example oligomers, homopolymers, copolymers of two or more monomers, and the like. The AEA may be natural or synthetic, and water insoluble or preferably water (saliva) soluble or swellable (hydratable, hydrogel forming). It has an (weight) average molecular weight of about 100 to about 1,000,000, or more, preferably about 1,000 to about 1,000,000, more preferably about 2,000 or 2,500 to about 250,000 or 500, 000. The description of AEA's in ancestor U.S. Pat. Nos. 5,032,386 and 5,192,530 is incorporated herein by reference.

The AEA contains at least one delivery-enhancing group, and at least one organic retention-enhancing group.

As employed herein, the delivery-enhancing group refers to one which attaches or substantively, adhesively, cohesively or otherwise bonds the AEA (carrying the antibacterial agent) to oral (e.g. tooth and gum) surfaces, thereby "delivering" the antibacterial agent to such surfaces. The organic retention-enhancing group, generally hydrophobic, attaches or otherwise bonds the antibacterial agent to the AEA, thereby promoting retention of the antibacterial agent to the AEA and indirectly on the oral surfaces.

Preferably, the AEA is an anionic polymer and especially a polycarboxylate of molecular weight or about 1,000 to about 1,000,000 or more comprising a chain or backbone containing repeating units each preferably containing at least one carbon atom and preferably at least one directly or indirectly pendent, monovalent delivery-enhancing group and at least one directly or indirectly pendant monovalent retention-enhancing group geminally, vicinally or less preferably otherwise bonded to atoms, preferably carbon, in the chain. Preferred polycarboxylates are often employed in the form of their free acids or preferably partially or more preferably fully neutralized water soluble or waterswellable (hydratable, gel-forming) alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether, having a molecular weight (M.W.) of about 30,000 to about 1,000,000, most preferably about 30,000 to about 500,000. These copolymers are available for example as Gantrez, e.g. AN 139 (M.W. 500,000); AN 119 (M.W. 250,000); and preferably S-97 pharmaceutical grade (M.W. 70,000), of GAF Corporation.

Organic surface-active agents are used in the compositions of the present invention to achieve increased prophylactic action. Moreover, they assist in achieving thorough and complete dispersion of the noncationic antibacterial agent throughout the oral cavity, and render the instant compositions more cosmetically acceptable. Indeed, at least one of surface-active agent or flavoring oil is present to effect desired solubilization of the antibacterial agent. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, higher fatty and esters of taurine and the substantially saturated higher aliphatic acyl amides of lower aliphatic amino carboxylic acid compounds, such as those having 12 to 16 carbons in the fatty acid, alkyl or acyl radicals, and the like. Examples of the last mentioned taurines and amides are N-methyl-N-cocoyl taurate, N-methyl-N-oleyl taurate, N-methyl-N-palmitoyl-taurate, N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarcosinate compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monostearate) and polypropyleneoxide (e.g. Pluronic materials).

Surface active agent is typically present in amount of about 0.5–5% by weight, preferably about 1–2.5%. As indicated, surface active agent is believed to assist in the dissolving of the noncationic antibacterial agents.

Various other materials may be incorporated in the oral preparations of this invention such as whitening agents, preservatives, silicones, chlorophyll compounds and/or ammoniated material such as urea, diamonium phosphate, and mixtures thereof. These adjuvants, where present, are incorporated in the preparations in amounts which do not substantially adversely affect the properties and characteristics desired.

Any suitable flavoring or sweetening material in addition to xylitol may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents for mixture with xylitol include sucrose, lactose, maltose, sorbitol, sodium cyclamate, perillartine, APM (aspartyl phenyl alanine methyl ester), saccharine and the like, with (sodium) saccharine being preferred. Suitably, flavor and sweetening agents (excluding xylitol, which is separately present) each or together comprise from about 0.1% to 5% more of the preparation. Moreover, flavor oil is believed to aid the dissolving of the antibacterial agent together with or even in the absence of surface-active agent.

Additional materials which substantially dissolve the antibacterial agent, to permit its delivery to the soft tissues at or near the gumline, may be employed in the present invention. Typical solubilizing materials include the humectant polyols such as propylene glycol, dipropylene glycol and hexylene glycol, cellosolves such as methyl cellosolve and ethyl cellosolve, vegetable oils and waxes containing at least about twelve carbon atoms in a straight chain such as olive oil, castor oil, and petrolatum and esters such as amyl acetate, ethyl acetate, glyceryl tristearate and benzyl benzoate. Propylene glycol is preferred. As used herein, "propylene glycol" includes 1,2-propylene glycol and 1,3-propylene glycol.

When the amount of substantially water-insoluble noncationic antibacterial agent is low, say up to about 0.3% by weight, as little as about 0.5% by weight of the foregoing solubilizing agent can be sufficient to solubilize the antibacterial agent. When higher amounts such as at least about 0.5% by weight, of antibacterial agent are present, it is desirable that at least about 5% by weight, typically up to about 20% or more by weight, of the solubilizing agent be present. These amounts may be considered to be a part of the liquid vehicle of the dentifrice and in fact the solubilizing agents include polyol humectants such as propylene glycol and dipropylene glycol.

In the preferred practice of this invention an oral composition containing the composition of the present invention is preferably applied regularly to dental enamel, such as every day or every second or third day or preferably from 1 to 3 times daily, at a pH of about 4.5 to about 9 or 1 0, generally about 5.5 to about 8, preferably about 6.5 to 7.5 or 8, for at least two weeks up to eight weeks or more up to lifetime.

It will be understood that, as is conventional, the oral preparations are to be sold or otherwise distributed in suitable labeled packages. Thus a toothpaste or dental cream or gel dentifrice as well as a dental gel will usually be in a collapsible tube typically aluminum, lined lead or plastic, or other squeeze, pump or pressurized dispenser for metering out the contents, having a label describing it, in substance, as a toothpaste, dental cream or the like. A mouth rinse will generally be in a glass or plastic bottle.

The following examples are further illustrative of the nature of the present invention, but it is understood that the invention is not limited thereto. All amounts and proportions referred to herein and in the appended claims are by weight, unless otherwise indicated.

EXAMPLE 1

The following opacified dentifrice is prepared:

|  | Parts By Weight |
| --- | --- |
| Triclosan | 0.30 |
| Xylitol | 10.00 |
| Silica Polishing Agent (Zeodent 113) | 20.00 |
| Glycerin | 15.00 |
| Gantrez S97 (13.37%) | 15.00 |
| Sorbitol (70%) | 14.50 |
| Silica Thickener (Sylox 15) | 2.00 |
| Sodium Lauryl Sulfate | 1.50 |
| Sodium Hydroxide (50%) | 1.20 |
| Flavor | 1.00 |
| Sodium Carboxymethylcellulose | 0.80 |
| Propylene Glycol | 0.50 |
| Titanium Dioxide | 0.50 |
| Iota Carrageenan | 0.30 |
| Sodium Saccharin | 0.30 |
| Water | 17.10 |

An experiment conducted on rats is described as follows:

TABLE 1

Brief Summary of the Protocol

The rats are weaned (Day 20 after birth) and randomly distributed among two treatment groups of ten each. They are maintained on a cariogenic diet 2000 (56% sucrose, 28% skimmed milk powder, 8% wheat flour, 5% dried yeast, 2% Gerval Protein (Lederle Co.), and 1% NaCl) and de-ionized water ad libitum. On days 21 and 22, the rats are inoculated intra-orally, with a suspension of *Streptococcus mutans* OMZ176 and *Actinomyces viscous* Ny-1. Test dentifrices or solutions (0.1 mL) are applied twice daily by means of disposable syringes for the duration of the study. The extent of smooth-surface and fissure caries is assessed according to previously described methods (Schmid et al., 1984).

Results of Experimental Dentifrices on Dental Caries in Rats

|  | Mean Caries Incidence per Rat (N = 10) | |
| --- | --- | --- |
| Treatment | Dentinal Fissures | Smooth Surfaces |
| Control, H$_2$O | 9.7 ± 1.83 | 14.8 ± 1.93 |
| Example 1 Dentifrice | 6.7 ± 4.32* | 15.0 ± 5.96 |

*Significantly different from control, P <0.05

The results of this study indicate that the experimental dentifrice is effective in reducing caries incidences in dentinal fissures of rats.

In addition, by including a fluoride providing agent such as 0.243 parts sodium fluoride or 0.76 parts of sodium monofluorophosphate in place of corresponding amount of water, smooth surface caries are also reduced.

EXAMPLE 2

The following translucent dentifrice is prepared:

|  | Parts By Weight |
| --- | --- |
| Triclosan | 0.30 |
| Xylitol | 10.00 |
| Silica Polishing Agent (Zeodent 113) | 20.00 |
| Glycerin | 15.00 |
| Gantrez S97 (13.37%) | 15.00 |
| Sorbitol (70%) | 14.50 |
| Silica Thickener (Sylox 15) | 2.00 |
| Sodium Lauryl Sulfate | 1.50 |
| Sodium Hydroxide (50%) | 1.20 |
| Flavor | 1.00 |
| Sodium Carboxymethylcellulose | 0.80 |
| Titanium Dioxide | 0.50 |
| Iota Carrageenan | 0.30 |
| Sodium Saccharin | 0.30 |
| Water | 17.60 |

EXAMPLE 3

The following opacified dentifrice is prepared:

|  | Parts By Weight |
| --- | --- |
| Triclosan | 0.30 |
| Xylitol | 10.00 |
| Silica Polishing Agent (Zeodent 113) | 20.00 |
| Glycerin | 15.00 |
| Sorbitol (70%) | 14.50 |
| Silica Thickener (Sylox 15) | 2.00 |
| Sodium Lauryl Sulfate | 1.50 |
| Sodium Hydroxide (50%) | 1.20 |
| Flavor | 1.00 |
| Sodium Carboxymethylcellulose | 0.80 |
| Propylene Glycol | 0.50 |
| Titanium Dioxide | 0.50 |
| Iota Carrageenan | 0.30 |
| Sodium Saccharin | 0.30 |
| Water | 32.10 |

EXAMPLE 4

The following mouthrinse is prepared:

|  | Parts by Weight |
| --- | --- |
| Triclosan | 0.03 |
| Xylitol | 1.0 |
| Ethanol | 10.0 |
| Propylene Glycol | 7.0 |
| Sorbitol | 10.0 |
| Glycerol | 10.0 |
| Sodium Lauryl Sulfate | 0.25 |
| Tauranol | 0.20 |
| Flavor | 0.10 |
| Water | Q.S. to 100.00 |

EXAMPLE 5

The following dental gel is prepared:

|  | Parts by Weight |
| --- | --- |
| Triclosan | 0.3 |
| Xylitol | 10.0 |
| Sodium Lauryl Sulfate | 0.6 |
| Flavor | 1.0 |
| Iota Carragunan | 0.65 |

-continued

|  | Parts by Weight |
| --- | --- |
| NaCMC | 2.0 |
| Glycerine | 20.0 |
| Propylene Glycol | 0.5 |
| Silica Thickener (Sylox 15) | 5.0 |
| Sorbitol | 15.0 |
| Tauranol | 0.25 |
| Sodium Saccharine | 0.1 |
| Sodium Fluoride | 0.243 |
| Water | Q.S. to 100.00 |

This invention has been described with respect to certain preferred embodiments and it will be understood that modifications and variations thereof obvious to those skilled in the art are to be included within the purview of this application and the scope of the appended claims.

We claim:

1. An antimicrobial oral composition which has anticaries effectiveness in reducing caries incidence in dentinal fissures even without a fluoride ion source essentially comprising an aqueous humectant vehicle, and when said oral composition is a dentifrice, about 10–30% by weight of a water-insoluble dentally acceptable siliceous polishing agent, said oral composition comprising an effective antiplaque active ingredient amount of a substantially water insoluble noncationic antimicrobial agent, an antibacterial-enhancing agent in amount of about 0.05–4% by weight and at least about 0.1% by weight of xylitol, said oral composition containing at least one of a surface active agent and a flavor oil to facilitate dispersion of said antibacterial agent in said composition.

2. The oral composition claimed in claim 1 wherein said antimicrobial agent is present in amount of about 0.01–5% by weight.

3. The oral composition claimed in claim 1 wherein xylitol is present in amount of about 0.1–5% by weight.

4. The oral composition claimed in claim 1 wherein xylitol is present is amount of about 3–25% by weight.

5. The oral composition claimed in claim 4 wherein xylitol is present in amount of about 5–20% by weight.

6. The oral composition claimed in claim 1 wherein xylitol is present in amount of about 20–40% by weight.

7. The oral composition claimed in claim 1 wherein said antibacterial-enhancing agent is a polycarboxylate.

8. The oral composition claimed in claim 1 wherein said oral composition additionally comprises about 0.5–5% by weight of an organic surface-active agent.

9. The oral composition claimed in claim 1 wherein said oral composition comprises about 0.1–5% by weight of a flavoring oil.

10. The oral composition claimed in claim 1 wherein said oral composition is a dentifrice comprising a dentally acceptable siliceous polishing agent.

11. The oral composition claimed in claim 1 wherein said oral composition is a mouthrinse and said mouthrinse comprises a non-toxic alcohol.

12. The oral composition claimed in claim 1 wherein said oral composition is a dental gel.

13. A method of inhibiting plaque formation comprising applying the oral composition claimed in claim 1 to dental enamel.

14. The oral composition claimed in claim 1 wherein said antibacterial agent is selected from the group consisting of halogenated diphenyl ethers, halogenated salicylanilides, benzoic acids, halogenated carbanilides and phenolic compounds.

15. The oral composition claimed in claim 14 wherein said antibacterial agent is a halogenated diphenyl ether.

16. The oral composition claimed in claim 15 wherein said antimicrobial agent is triclosan.

17. The oral composition claimed in claim 16 wherein said amount of said antimicrobial agent is about 0.3–0.5% by weight.

18. The oral composition claimed in claim 7 wherein said polycarboxylate is a 1:4 to 4:1 copolymer of maleic anhydride or acid with methyl vinyl ether.

19. The oral composition claimed in claim 18 wherein said copolymer has a molecular weight of about 30,000 to about 1,000,000.

* * * * *